US005938655A

United States Patent [19]

Bisch et al.

[11] Patent Number: 5,938,655

[45] Date of Patent: Aug. 17, 1999

[54] REMOTE CONTROL WITH VARYING CODES

[75] Inventors: Michael Evremonde Bisch, St. Louis, Mo.; Christopher Michael Eberhardt, Ft. Worth, Tex.; John Alan Ritter, Des Peres, Mo.

[73] Assignee: Storz Instrument Company, St. Louis, Mo.

[21] Appl. No.: 08/919,546

[22] Filed: Aug. 28, 1997

Related U.S. Application Data

[60] Provisional application No. 60/025,498, Aug. 29, 1996.

[51] Int. Cl.[6] .......... A61B 17/00

[52] U.S. Cl. .......... 606/1; 341/176

[58] Field of Search .......... 606/1; 341/175, 341/176, 173; 607/60; 345/113, 4

[56] References Cited

U.S. PATENT DOCUMENTS

| | | | |
|---|---|---|---|
| 5,249,121 | 9/1993 | Baum et el. | 364/413.01 |
| 5,528,230 | 6/1996 | Kim | 341/176 |
| 5,786,784 | 7/1998 | Gaudichon | 341/176 |

*Primary Examiner*—Michael Buiz
*Assistant Examiner*—Jilian W. Woo
*Attorney, Agent, or Firm*—Grant D. Kang

[57] ABSTRACT

A system for controlling a plurality of ophthalmic microsurgical instruments connected thereto. The microsurgical instruments are for use by a user such as a surgeon in performing ophthalmic surgical procedures. The system includes a data communications bus and a user interface connected to the data communications bus. The user interface provides information to the user and receives information from the user which is representative of operating parameters of the microsurgical instruments. The system also includes surgical modules connected to and controlling the microsurgical instruments as a function of at least one of the operating parameters. The surgical modules are also connected to the data communications bus. The data communications bus provides communication of data representative of the operating parameters between the user interface and the surgical modules. Other features are also disclosed including a main control, an endo-illuminator system, a phacoemulsification handpiece, surgical scissors, a vitrectomy cutter, a surgical foot control, a remote control, a cart.

9 Claims, 15 Drawing Sheets

Microfiche Appendix Included
(31 Microfiche, 6067 Pages)

REMOTE CONTROL WITH VARYING CODES

MICROPHICHE APPENDIX

This application includes a microfiche appendix which is a copy of the provisional application 60/0245,498 filed Aug. 29, 1996 under which priority is claimed and updated source code.

BACKGROUND OF THE INVENTION

The invention generally relates to remote controls with security features which prevent false activation and, in particular, an infrared remote control employing alternating codes for controlling a microsurgical system.

Present day ophthalmic microsurgical systems provide one or more surgical instruments connected to a control console. The instruments are often electrically or pneumatically operated and the control console provides electrical or fluid pressure control signals for operating the instruments. The control console usually includes several different types of human actuable controllers for generating the control signals supplied to the surgical instruments. Often, the surgeon uses a foot pedal controller to remotely control the surgical instruments.

The conventional console has push-button switches and adjustable knobs for setting the desired operating characteristics of the system. The conventional control system usually serves several different functions. For example, the typical ophthalmic microsurgical system has anterior and/or posterior segment capabilities and may include a variety of functions, such as irrigation/aspiration, vitrectomy, microscissor cutting, fiber optic illumination, and fragmentation/emulsification.

While conventional microsurgical systems and ophthalmic systems have helped to make microsurgery and ophthalmic surgery possible, these systems are not without drawbacks. Microsurgical and ophthalmic systems are relatively costly and are often purchased by hospitals and clinics for sharing among many surgeons with different specialties. In eye surgery, for example, some surgeons may specialize in anterior segment procedures, while other surgeons may specialize in posterior segment procedures. Due to differences in these procedures, the control system will not be set up with the same operating characteristics for both procedures. Also, due to the delicate nature of eye surgery, the response characteristics or "feel" of the system can be a concern to surgeons who practice in several different hospitals, using different makes and models of equipment.

U.S. Pat. Nos. 4,933,843, 5,157,603, 5,417,246 and 5,455,766, all of which are commonly assigned and the entire disclosures of which are incorporated herein by reference, disclose improved microsurgical control systems. For example, such systems provide improved uniformity of performance characteristics, while at the same time providing enough flexibility in the system to accommodate a variety of different procedures. The systems shown in these patents improve upon the prior art by providing a programmable and universal microsurgical control system, which can be readily programmed to perform a variety of different surgical procedures and which may be programmed to provide the response characteristics which any given surgeon may require. The control system is preprogrammed to perform a variety of different functions to provide a variety of different procedures. These preprogrammed functions can be selected by pressing front panel buttons.

In addition to the preprogrammed functions, these patents disclose providing each surgeon with a programming key, which includes a digital memory circuit loaded with particular response characteristic parameters and particular surgical procedure parameters selected by that surgeon. By inserting the key into the system console jack, the system is automatically set up to respond in a familiar way to each surgeon.

For maximum versatility, the console push buttons and potentiometer knobs are programmable. Their functions and response characteristics can be changed to suit the surgeons' needs. An electronic display screen on the console displays the current function of each programmable button and knob as well as other pertinent information. The display screen is self-illuminating so that it can be read easily in darkened operating rooms.

Although the above-described systems provide improvements over the prior art, further improvements are needed to improve performance, simplify operation, simplify repair and replacement, reduce the time and cost of repairs, and so forth.

Medical sites such as operating rooms, out-patient surgery rooms, procedure rooms and clinics commonly have electronic equipment such as television monitors, video cassette recorders and stereos, each of which has its own infrared remote control to allow convenient control of their operation. These medical sites may also have microsurgical or other medical systems, such as ophthalmic machines, which also employ infrared remote controls so that a doctor or surgeon can remotely control the machine's operation. It is common for the electronic equipment to use standard commercial encoding formats, such as a Manchester encoded data stream, to transmit code so that, for instance, a single remote control might be used for several different systems by changing the code transmitted. However, there is no consensus which constrains certain codes to certain systems or classes of systems, and manufacturers are free to choose any code, at their discretion. It is imperative that remote controls for medical systems use adequate security techniques to ensure that operation of one of the remote controls for electronic equipment do not cause inadvertent actuation or deactivation of some medical system function, nor any change in control setting of a particular function of the medical system.

Many prior art medical systems have employed proprietary or complicated encoding schemes to avoid false activation. However, such schemes are expensive to develop and implement and cannot be implemented with off-the-shelf remote control IR encoding ICs.

Other prior art medical systems have used extended codes, such as 32 bit or longer codes, to minimize the possibility of two systems using the same code. However, such extended codes reduce battery life in the remote because of the extended transmission time required and there is no guarantee that a particular code will be unique.

SUMMARY OF THE INVENTION

The invention comprises an apparatus for use by an operator for remotely controlling a system, particularly an ophthalmic microsurgical system. A transmitter has a keypad having keys which the operator controls by activating the keys. The transmitter is responsive to the keypad for transmitting first and second signals, each of the signals including a function code defined by the particular key activated by the operator and including an additional code wherein the function code of the first and second signals is the same and wherein the additional code of the first signal is different from the additional code of the second signal. A receiver receives the first and second signals transmitted by the transmitter. The receiver is associated with the system for providing functional control signals to the system for controlling functions of the system according to the function codes transmitted by the transmitter. The receiver provides functional control signals to the system only when the additional code of the first signal is different from the additional code of the second signal.

Other objects and features will be in part apparent and in part pointed out hereinafter.

BRIEF DESCRIPTION OF THE DRAWINGS

FIG. 6*a*, 6*b*, 6*c* and 7 and 8 are flow diagrams of software operating the microcontroller controlling the transmitter of FIG. 2;

DETAILED DESCRIPTION OF THE PREFERRED EMBODIMENTS

Figure 1:
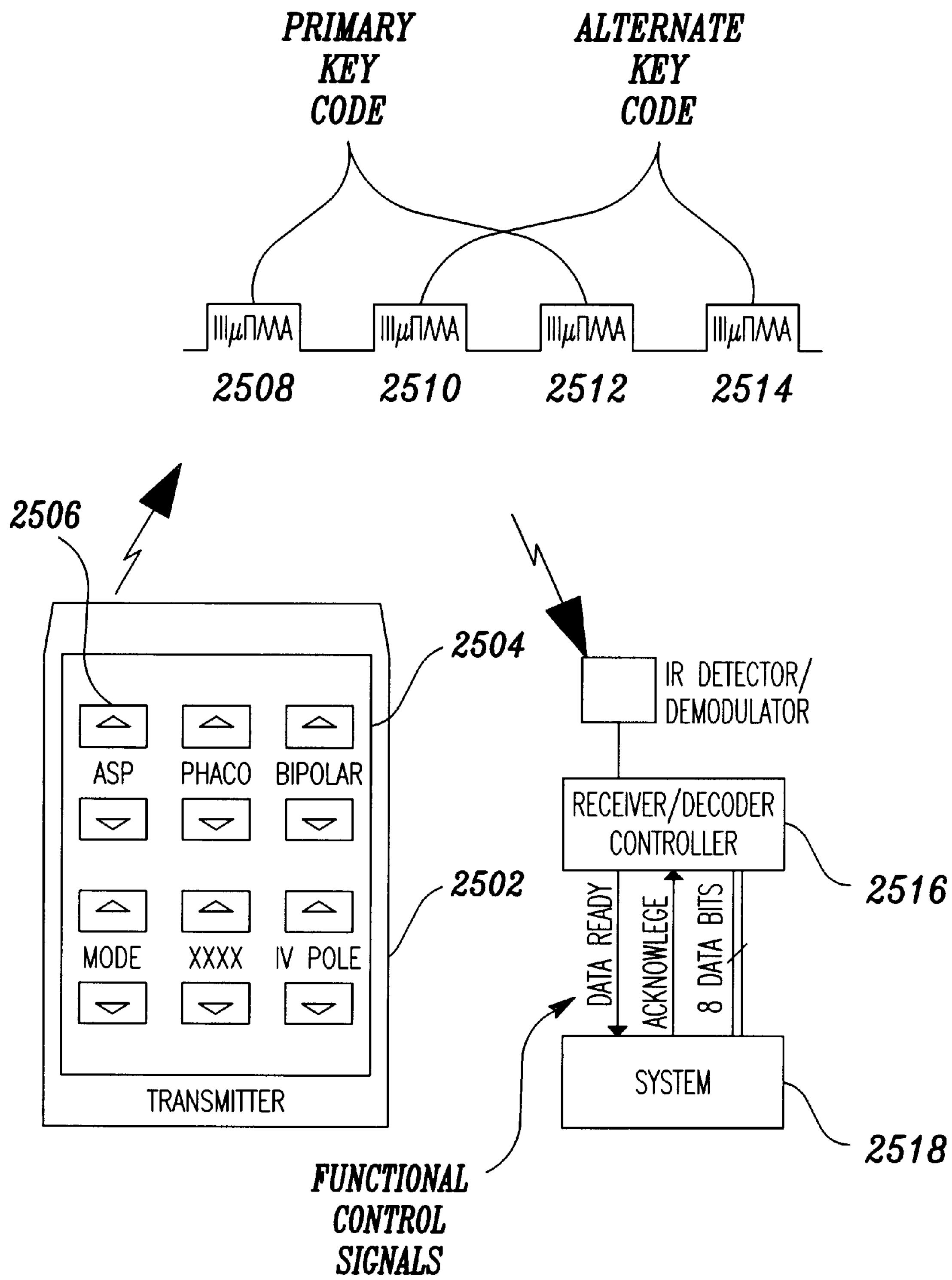
FIG. 1 is a block diagram of a remote control with varying codes according to the invention.

Referring to FIG. 1, a block diagram of a remote control with varying codes according to the invention is illustrated. A hand held remote control transmitter 2502 includes a keypad 2504 having keys 2506 which an operator controls by depressing or otherwise activating the keys. As illustrated in FIG. 1, the keys 2506 may be generic keys (e.g., up, down, left, right, and stop keys) or may be dedicated keys as illustrated in FIGS. 2*a*, 2*b*, and 2*c* and 10. The transmitter 2502 is responsive to a depressed key for transmitting a signal, such as an infrared (IR) signal, having a series of successive, contiguous data streams 2508, 2510, 2512 and 2514. The specific format of the data stream according to the invention is described below with regard to FIGS. 3 and 5. In general, each of the data streams includes a function code. For example, as illustrated in FIG. 1, each of the data streams include an "UP" pulse indicating that the operator has depressed an UP key of the keypad 2504. In other words, the function code is defined by the particular key activated by the operator. In addition, each of the data streams includes an additional code according to the invention so that data streams 2508 and 2512 include a primary code, or code A, and data streams 2510 and 2514 include a secondary code, or code B. As a result, the transmitter 2502 incorporates a transmission scheme in which one or more bits of serially transmitted code are varied between predetermined values on successive data stream transmissions in response to the same function key.

As is well known, the transmitted signals may be infrared (IR) signals so that a receiver 2516 includes an IR receiver circuit (such as circuit 267 illustrated in FIG. 8) for receiving the IR signals transmitted by the hand-held remote control transmitter 2502. In particular, the receiver 2516 includes a demodulator for decoding the IR signals and a controller such as a microcontroller or a dedicated logic circuit or chip for evaluating the decoded signals and providing functional control signals to the system 2518. The receiving circuit 2516 first verifies that the IR signal received includes a legitimate function code and second, that the function code of the next IR signal received is the same as the previous, but with the additional code of alternating bits in the proper states for the "alternate transmission" according to the invention (see FIG. 9). Only when both conditions are met will a valid received code be reported. The receiver 2516 is associated with the system 2518 (such as a microsurgical control system). Receiver 2516 provides the functional control signals to the system 2518 for controlling functions of the system according to the function codes transmitted by the transmitter 2502. For example, receiver 2516 may provide up, down, left, right, and stop functional control signals to system 2518. As noted above, the receiver 2516 provides functional control signals to the system 2518 only when the additional code (A or B) of a first received signal is different from the additional code (B or A) of a second received signal.

Figure 2A:
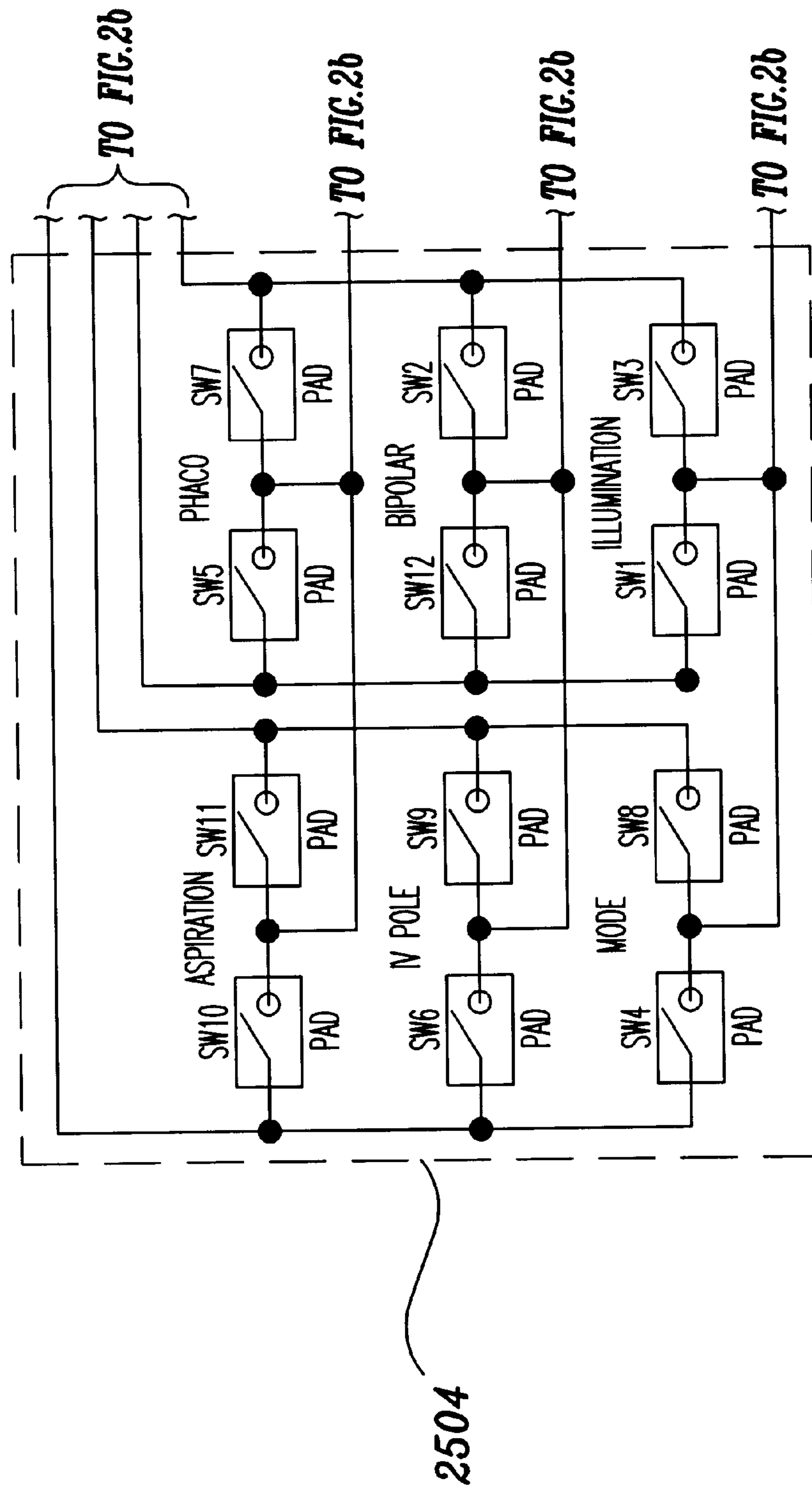
FIG. 2*a*, 2*b*, and 2*c* is a schematic diagram of one preferred embodiment of an infrared remote control transmitter employing alternating codes according to the invention, particularly for providing signals to be received by a receiver for controlling a ophthalmic microsurgical system.
Figure 2B:
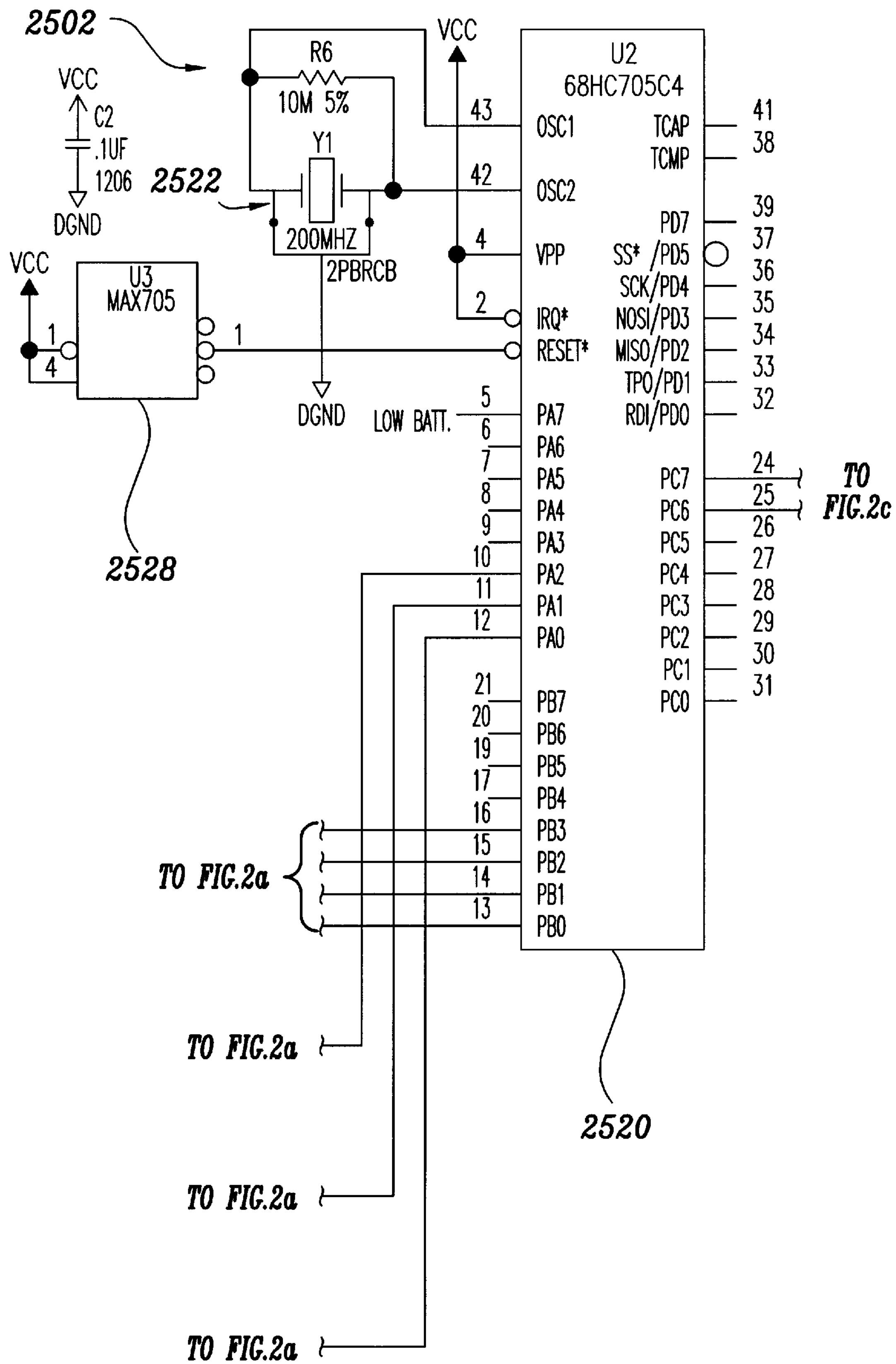
Figure 2C:
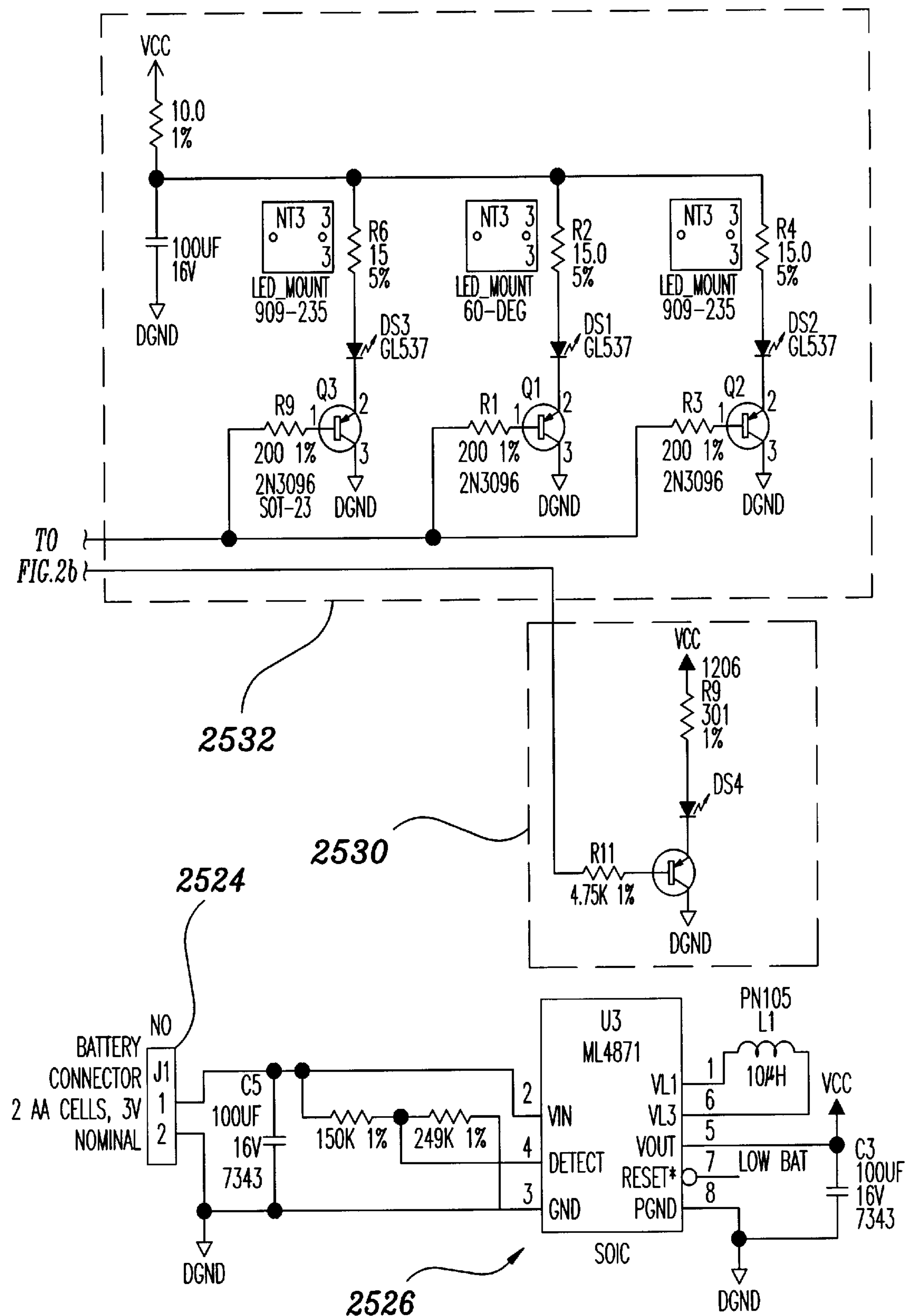

FIG. 2*a*, 2*b*, and 2*c* illustrates a schematic diagram of one preferred embodiment of the infrared remote control transmitter 2502 employing alternating codes according to the invention, particularly for providing signals to be received by a receiver for controlling the ophthalmic microsurgical system (generally designated 1). This embodiment includes a single chip microcontroller 2520, such as a Motorola MC68HC705C4, to perform the keypad scanning and IR encoding functions. Microcontrollers and particularly this microcontroller allow full control over the firmware for the chip so that a security system can be implemented which varies several bits of the transmitted code on successive repetitions of a given key encoding. As shown in FIG. 2*a*2*b*, and 2*c* the transmitter 2502 includes a keypad 2504 having 12 keys or switches which allow up/down aspiration, phaco, IV pole, bipolar, mode, and illumination control. An oscillator 2522 controls the timing of the microcontroller 2520. Preferably, the unit is battery powered by a battery 2524 connected to a circuit 2526 for conditioning its output voltage and generating a VCC voltage which is applied to a power on reset chip 2528 for automatically resetting the microcontroller 2520 when the battery is changed. In addition, the VCC voltage is applied to the microcontroller 2520 to drive it and is applied to a low battery indicator circuit 2530. The VCC voltage also drives an infrared transmitting circuit 2532 which includes three IR light emitting diodes for simultaneously generating the infrared signal to be provided to receiver 2516.

Figure 3:
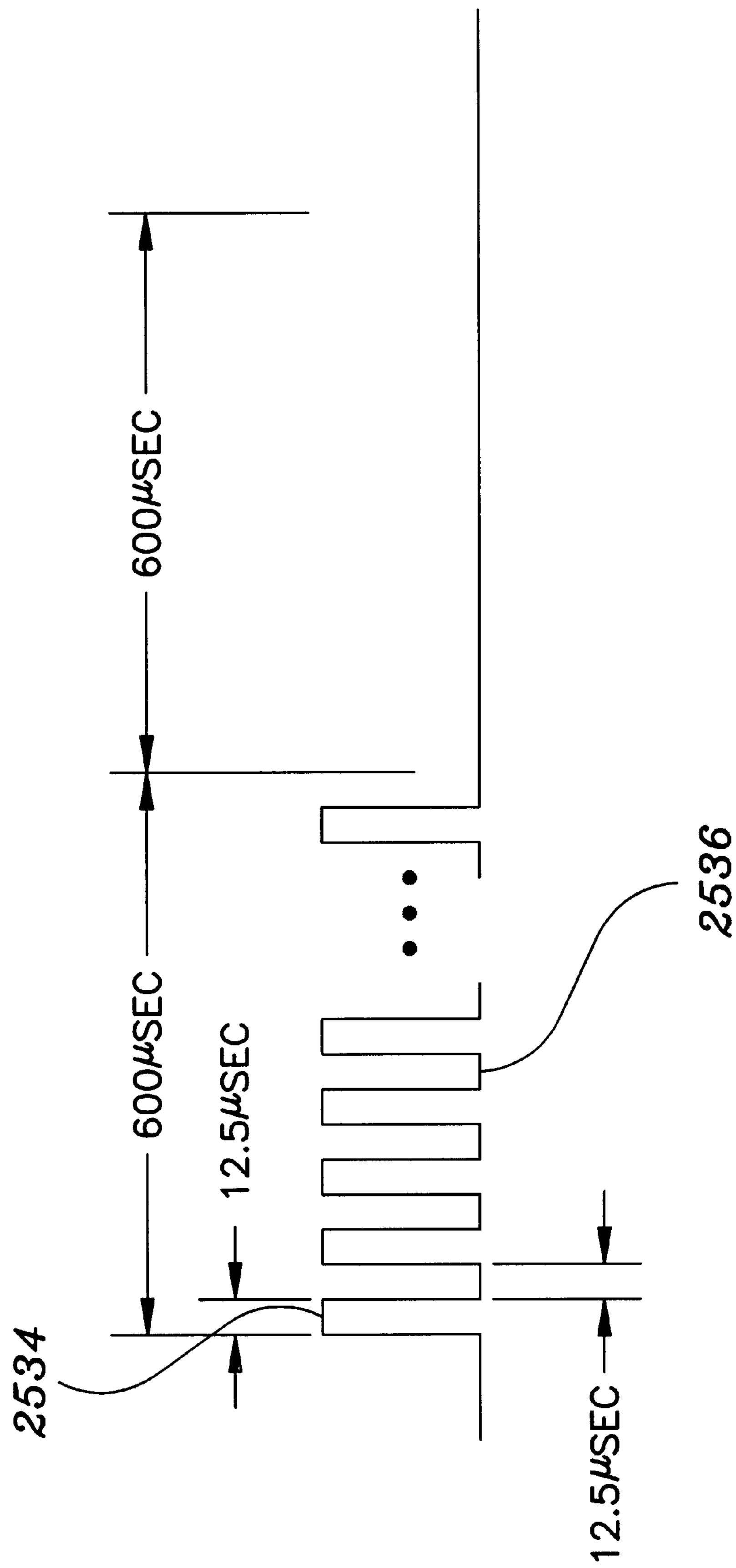
FIG. 3 is a waveform diagram of the bits of the data streams transmitted by the transmitter of FIG. 2.
Figure 4:
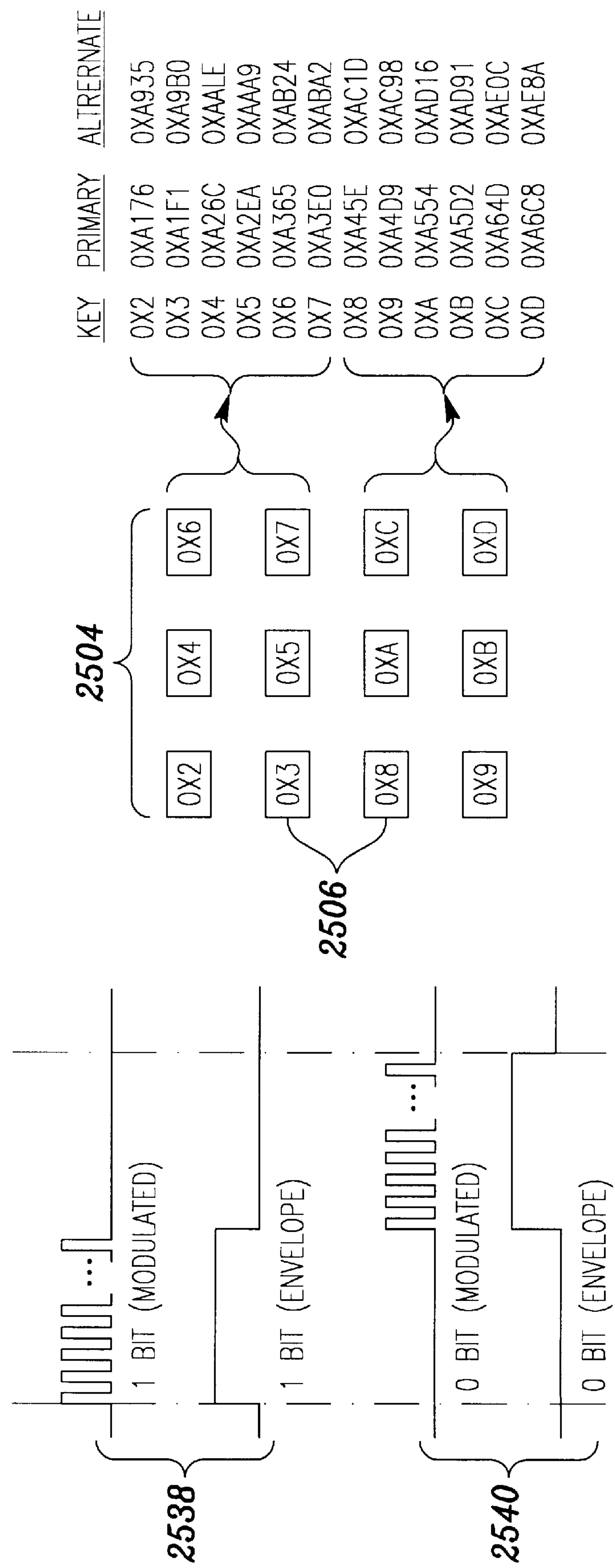
FIG. 4 is an illustration of a 12 key keypad and including a table showing the primary and alternate ASCII codes corresponding to each of the keys.

FIG. 3 illustrates a timing diagram of the waveform of each bit of the data stream transmitted by the transmitter 2502 of FIG. 2*b*. Each bit 2538, 2540 is 400 microseconds in length including a modulated signal having pulses 12.5 microseconds in length immediately followed by spaces of the same length. The "1" bit 2538 includes a 600 microsecond modulated envelope followed by a mid-bit transition to a 600 microsecond space whereas the "0" bit 2540 is a 600 microsecond space followed by mid-bit transition to a 600 microsecond modulated envelope of 24 pulses and spaces. As shown in FIG. 4, there are twelve keys or switches of the keypad 2504 which may be depressed by the operator. Each of the twelve keys 2506 has a primary code and an alternate code as illustrated in the table of FIG. 4.

Figure 5:
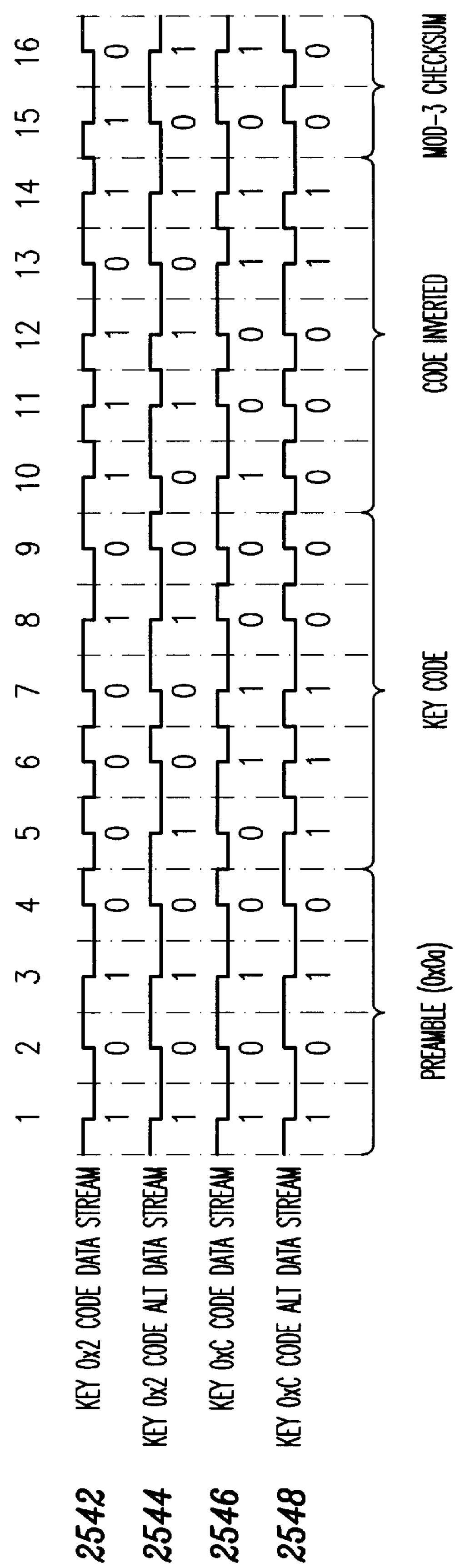
FIG. 5 is a waveform diagram of various 16 bit data streams transmitted by the transmitter of FIG. 2.

As shown in FIG. 5, each data stream includes 16 bits of information. Data stream 2542 is the primary code data stream corresponding to activation of key 0x2 as defined by the primary code 0xa176. Data stream 2544 is the secondary code data stream corresponding to activation of key 0x2 as defined by the alternate code 0xa935. Data stream 2546 is the primary code data stream corresponding to activation of key 0xc as defined by the primary code 0xa64d. Data stream 2548 is the secondary code data stream corresponding to activation of key 0xc as defined by the alternate code 0xae0c.

The first four bits 1–4 comprise a synchronization preamble and would usually be the same for each data stream being transmitted. As illustrated in FIG. 5, each of the data streams includes a preamble of four bits comprising "1010."

The preamble is followed by one bit which is the additional code bit which alternates with each successive transmission of a data stream corresponding to the same function key. Data stream 2542 comprises the primary data stream of key 0x2 and data stream 2544 comprises the alternate data stream of key 0x2. Bit 5 is "0" for primary data stream 2542 and alternates to a "1" for alternate data stream 2544.

The additional code bit 5 is followed by four bits 6–9 which define the function of the particular key which has been activated. Data stream 2542 is the primary code data stream corresponding to key 0x2 and includes four bits comprising "10010". Data stream 2544 illustrates the alternate data stream or the second data stream that is transmitted when the 0x2 key continues to remain activated resulting in the function code comprising "0010" being transmitted again.

For each data stream, bits 10–14 comprise a logical transformation of the additional code bit 5 and the function code bits 6–9. In particular, bits 10–14 comprise the inverted code transmitted as bits 5–9. Finally, each data stream ends with a modulo-three check sum of two bits 15, 16. This encoding scheme, with the specific function code contained twice in different but logically related forms minimizes the chances of false or errant activation by another transmission. In addition, the check sum ensures against codes being incorrectly recognized due to interference or other transmission/reception errors.

Similarly, data stream 2546 comprises the primary data stream of key 0xc and data stream 2548 comprises the alternate data stream of key 0xc. Data stream 2546 includes a four bit preamble of 1010, and an additional code bit 5 which a "0", a four bit function code of "1100". This is followed by bits 10–14 which are the inverted version of bits 5–9, i.e., 10011, which is then followed by check sum 01. As key 0xC continues to remain depressed, the alternate data stream is next transmitted as illustrated by data stream 2548 including preamble 1010, additional bit 1, function code 1100, inverted bits 00011 and check sum 00.

In summary, the essential difference between primary data stream 2542 and alternate data stream 2544 is bit 5 which alternates from 0 to 1 and the resulting change in the check sum of bits 15 and 16 from "10" to "01". Similarly, the essential difference between primary data stream 2546 and alternate data stream 2548 is bit 5 which alternates from 0 to 1 and the resulting change in the check sum of bits 15 and 16 from "01" to "00".

In one preferred embodiment, the primary data stream is again transmitted after the alternate data stream so that the data stream for each depressed key comprises a data stream corresponding to the primary code for the key followed by a data stream corresponding the alternate code for the key followed by a data stream corresponding to the primary code for the key followed by a data stream corresponding to the alternate code for the key, and so on. However, it is contemplated that more than two different key codes or additional alternating bits could be successively transmitted to further enhance the security aspects of the system. For example, first, second, and third codes could be successively transmitted and would need to be transmitted in order to be verified by the receiver 2516. Those skilled in the art would recognize other alternatives as well, such as pseudorandom alternating bits.

The preamble of "1010" illustrates one technique for synchronizing a Manchester encoded data stream, since the sequence contains only the mid-bit transitions. The purpose of the modulo-three check sum is to guard against any single-bit errors which might occur. On alternate transmissions, additional bit 5 and its inverted bit 10 of each data stream are inverted so that the check sum value of bits 15 and 16 will be different. This ensures at least three bits difference (four for some check sum values) between successive primary and alternate data streams transmitted and provides ample security against random triggering by other commercial remote controls which may be operated in the vicinity.

Figure 6A:
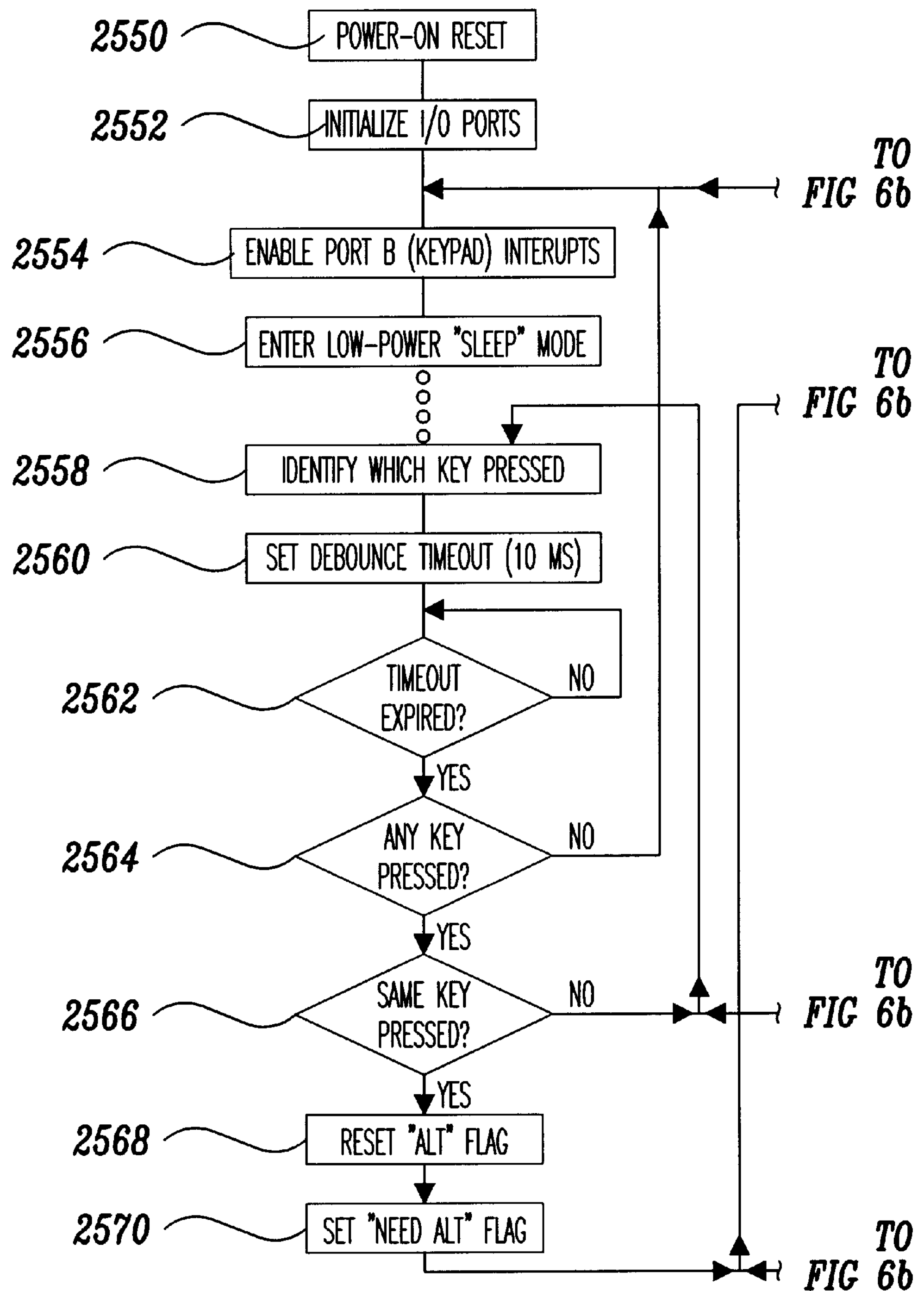
Figure 6B:
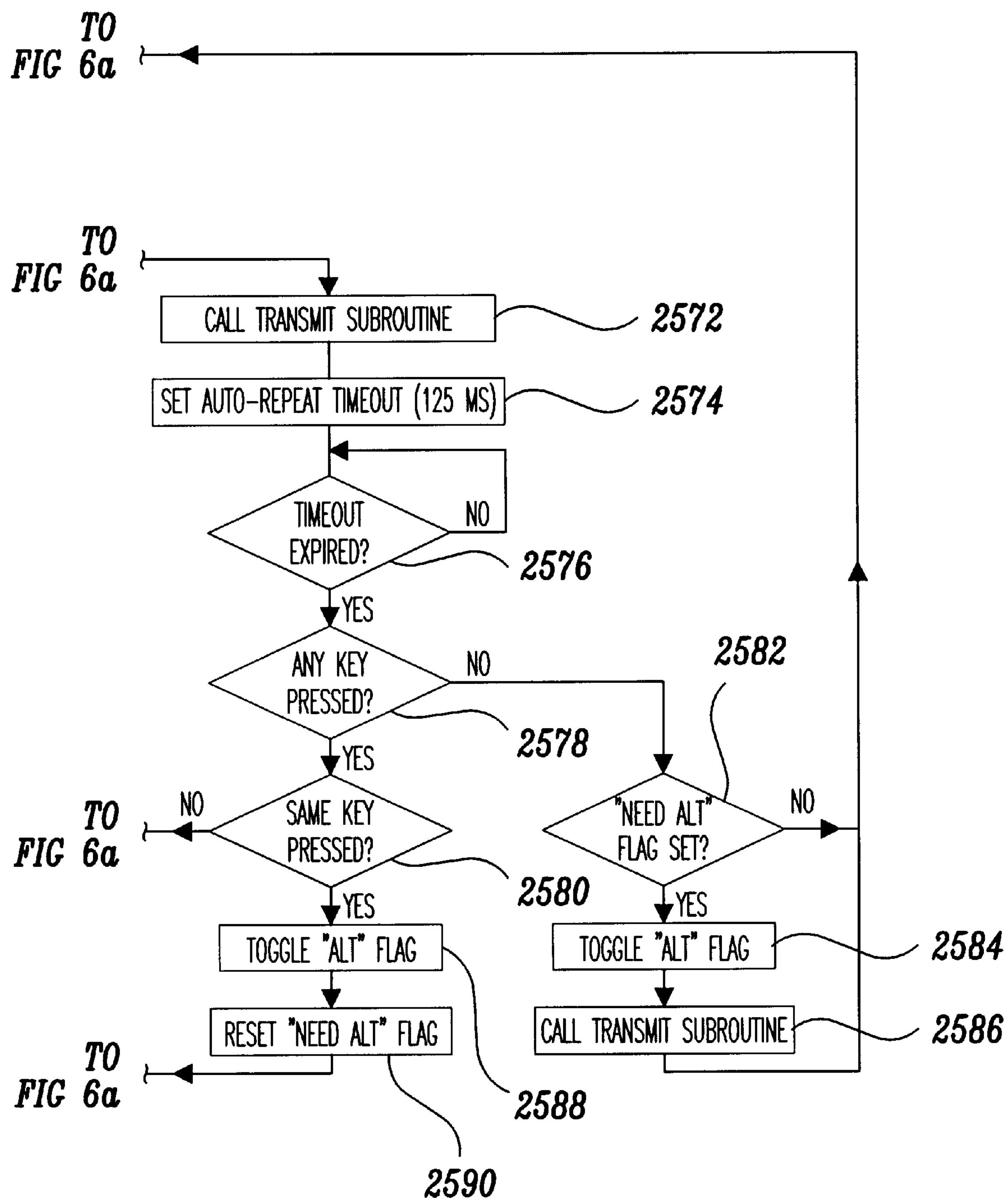

FIG. 6*a*and 6*b* is a flow diagram of the software operating the microcontroller 2520 of FIG. 2*b*. After the batteries are added to the remote control, the microcontroller responds to reset chip 2528 and the software executes a power-on reset at step 2550 followed by initializing of the input/output ports of the microcontroller 2520 at step 2552. Thereafter, the microcontroller enables the port B (keypad) interrupts at step 2554 and, if no keys are depressed, enters the low-power "sleep" mode at step 2556. When a key is depressed, the interrupt service routine of FIG. 7 disables further interrupts and returns to step 2558 that identifies which key has been depressed. The dotted line between steps 2556 and 2558 represents this transition and is traversed as a result of a key being depressed and the interrupt service routine executing the RTI. Basically, the microcontroller 2520 has a STOP instruction which puts it in a deep power down mode. An interrupt from the keypad 2504 brings it out of this state, and when the interrupt service routine ends, execution of the software continues with the first instruction after the STOP.

Step 2560 sets a debounce time out for 10 milliseconds which is a minimum period of time a key must be depressed in order to continue execution of the software. Step 2562 times out the set time and the microcontroller again checks at step 2564 to see if the key is still being depressed and the switch corresponding thereto is still closed. If step 2564 finds no key has been depressed, the routine returns to step 2554. Step 2566 verifies that the same key has been depressed. If step 2566 finds that a different key has been depressed, the software returns to step 2558 to identify the key. Otherwise, constant depression of the same key results in an alternate flag being reset by step 2568 and a need alternate flag being set by step 2570.

The microcontroller then executes step 2572 to call the transmit routine and an auto repeat time out is set for 125 millisecond by step 2574. After this time out is complete, as determined by step 2576, the microcontroller again verifies that a key is being depressed by step 2578 and that the same key is being depressed is verified by step 2580. If the same key is not being depressed, the microcontroller returns to step 2558 to determine which key is being depressed. If step 2578 finds that no key is being depressed, step 2582 determines if the need alternate flag has been set. This is to determine whether the last data stream was a primary data stream so that the complementary alternate data stream must still be transmitted. If the need alternate flag has not been set, no complementary data stream transmission is needed and the microcontroller returns to step 2554 to wait for the next key to be depressed. If the flag has been set, it is toggled by step 2584 and the transmit routine is executed one more time by step 2586.

If the same key continues to remain depressed as determined by step 2580, the alternate flag is toggled by step 2588 and the need alternate flag is reset by step 2590. Then, the transmit sub-routine is again called by step 2572 and the cycle continues. Data streams of alternating additional codes and the same function code are transmitted until step 2580 determines that a different key has been depressed or step 2578 determines that no key is being depressed.

Figures 7, 8:
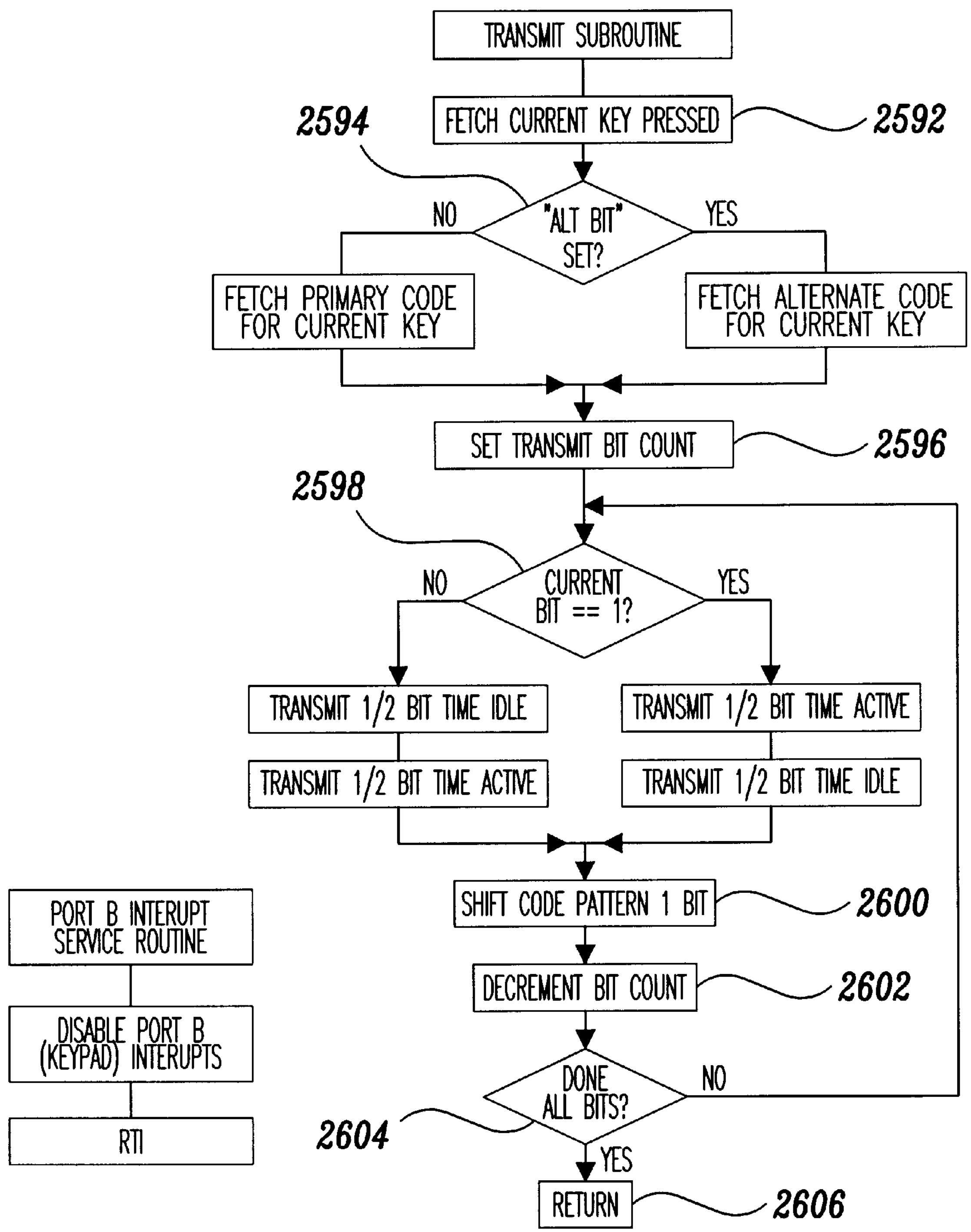

FIG. 8 illustrates the transmit sub-routine which is called and executed by steps 2572 and 2586. Step 2592 fetches or identifies the current key depressed and step 2594 fetches either the primary or alternate code depending on whether the alternate flag has been previously set. Step 2496 prepares to transmit the bit count. Step 2598 determines whether the bit to be transmitted is a "1" or a "0". Step 2598 transmits an active envelope followed by an idle time if the bit is 1 or transmits the inverse if the bit is 0. Step 2600 shifts to the next bit to be transmitted, step 2602 decrements the bit count and step 2604 returns to transmit the next bit by step 2598 unless all the bits have been transmitted. When all bits have been transmitted, the software instructs the microcontroller to continue with the main software routine of FIG. 6, which would be either step 2574 or step 2554.

Figure 9:
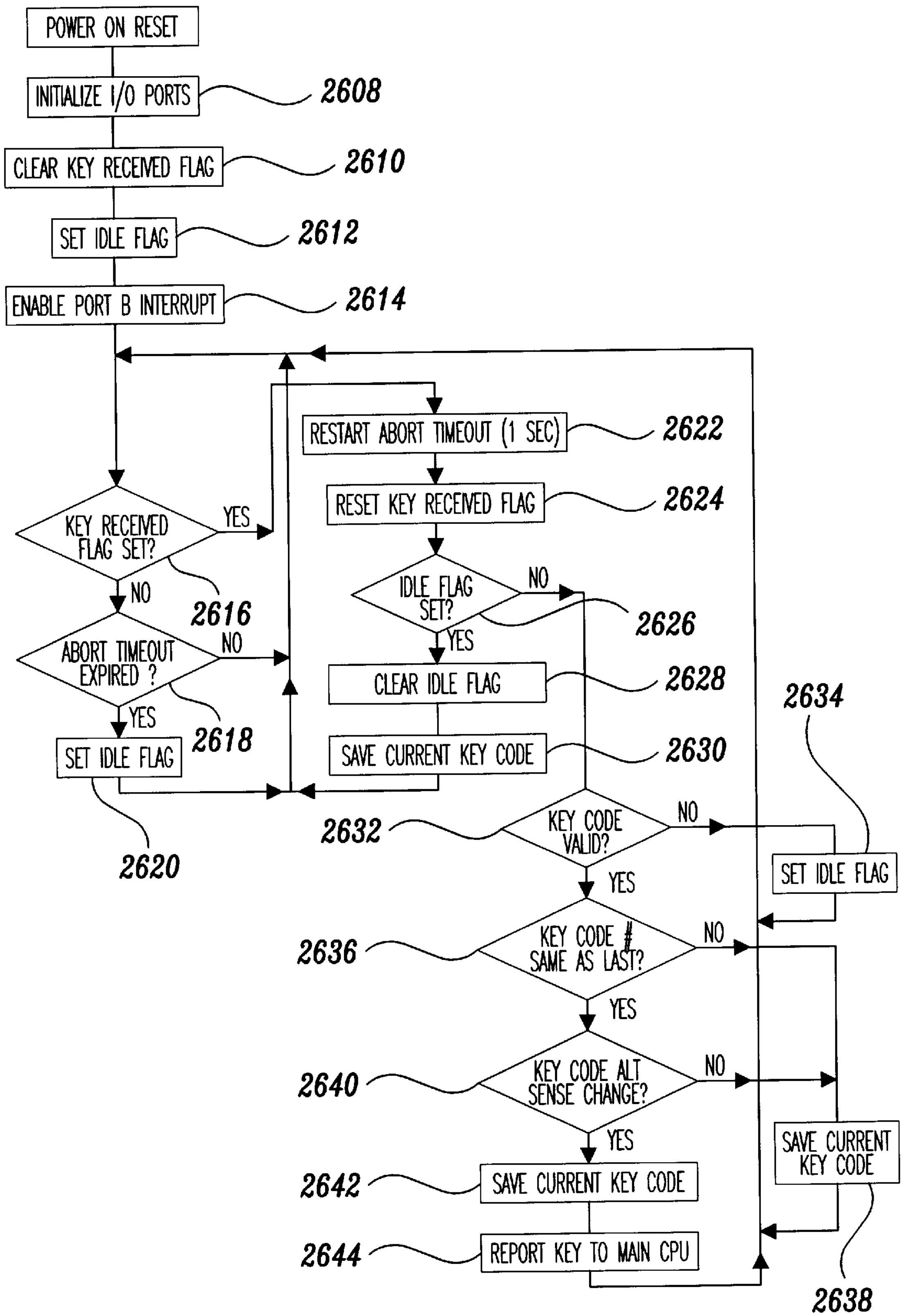
FIG. 9 is a flow diagram of software operating a microcontroller receiving output signals from a IR decoder receiving the signal from the transmitter of FIG. 2.
Figure 10A:
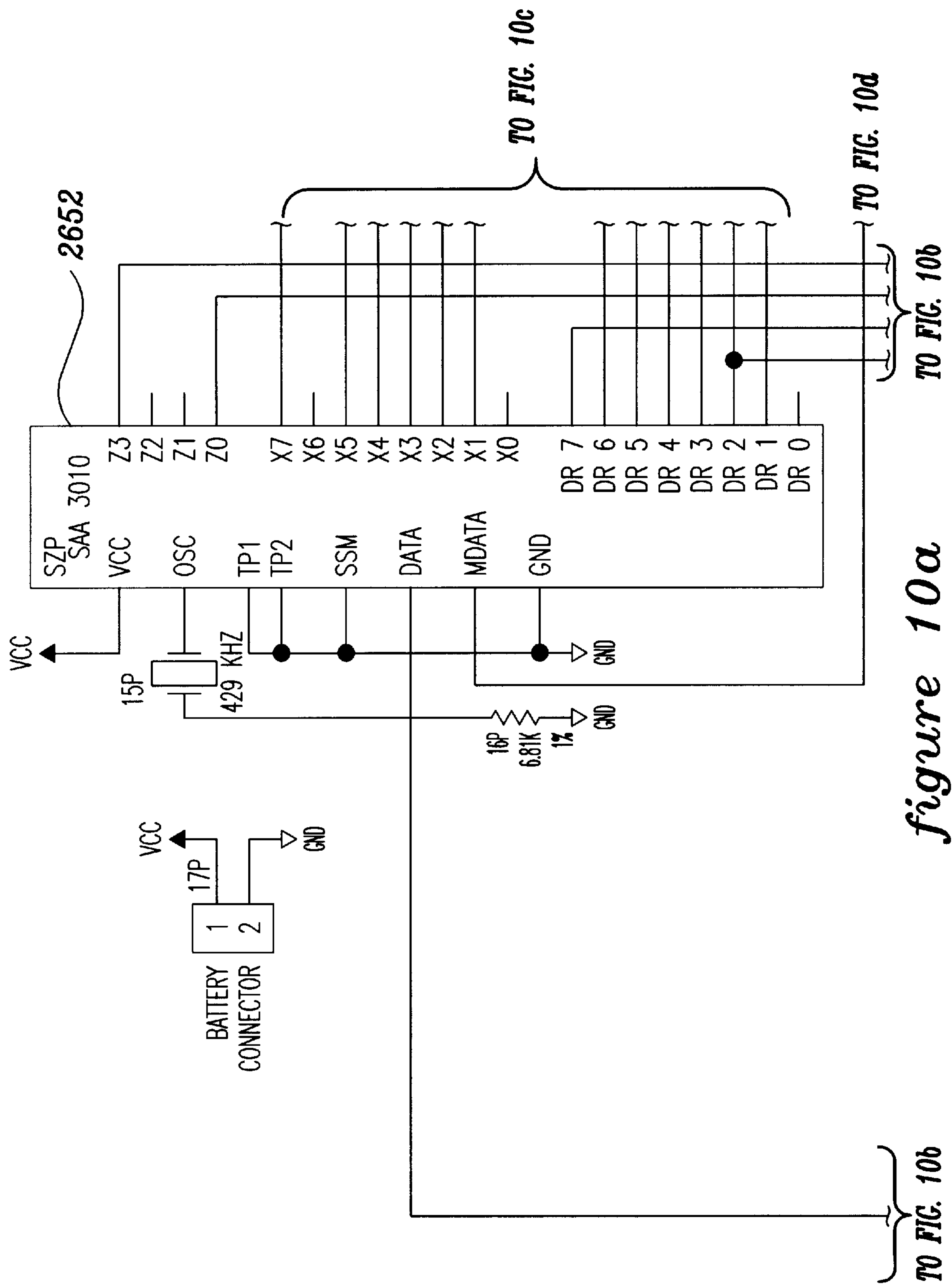
FIG. 10*a*, 10*b*, 10*c*, and 10*d* is a schematic diagram of another preferred embodiment of an infrared remote control transmitter employing alternating codes of the invention using logic circuitry to alternate between two different system codes on successive transmissions for providing signals to be received by a receiver for controlling a ophthalmic microsurgical system.
Figure 10B:
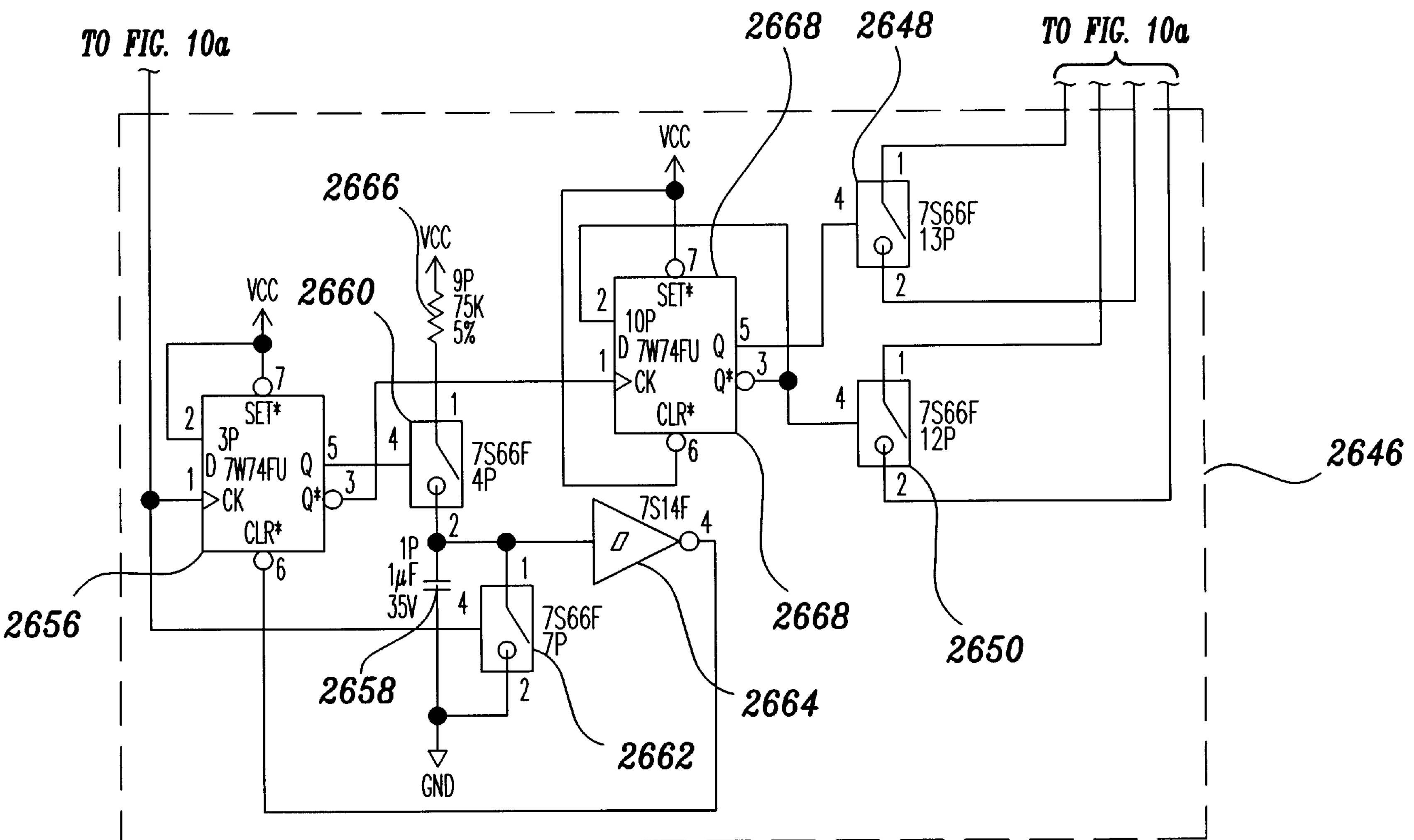
Figure 10C:
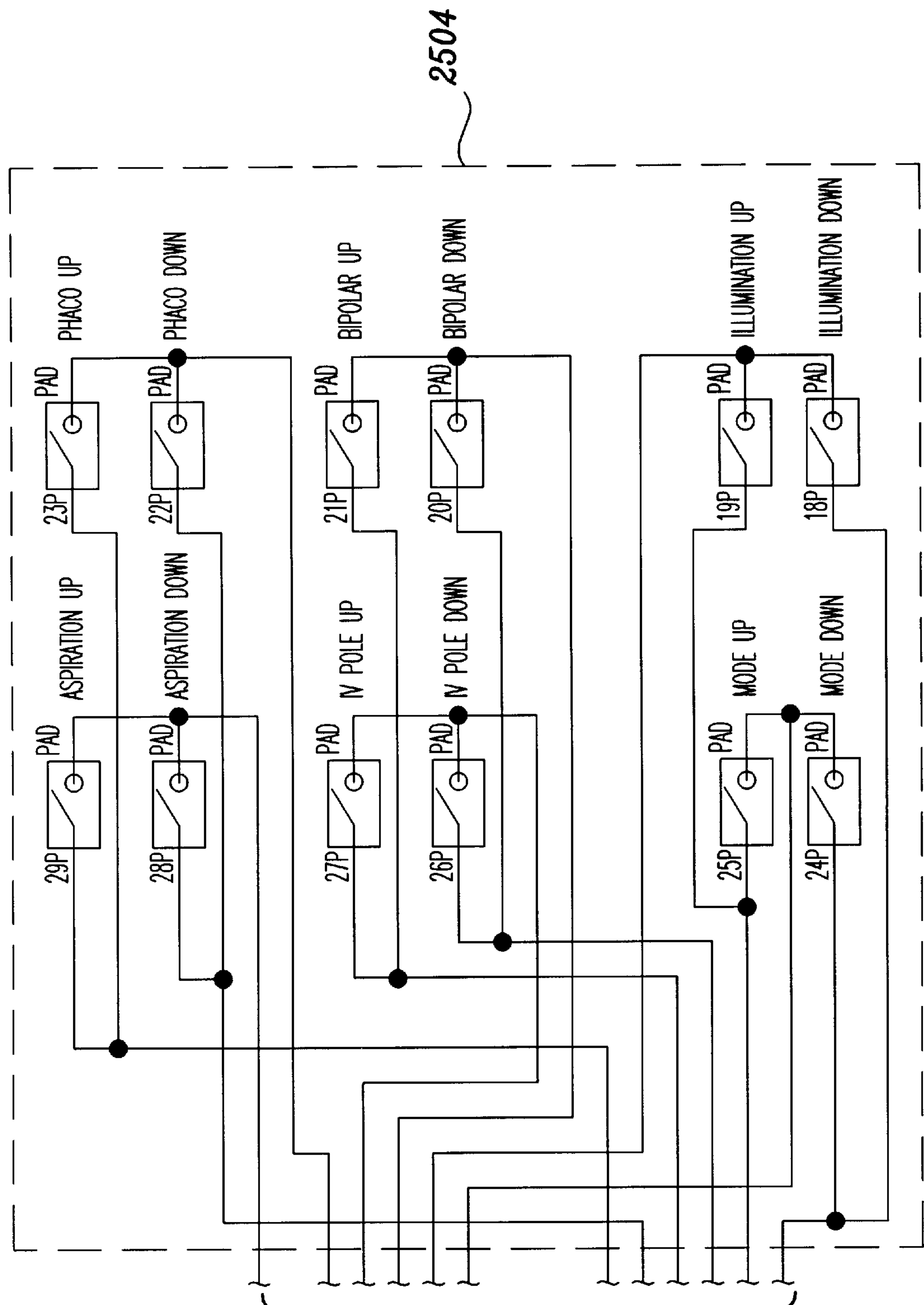
Figure 10D:
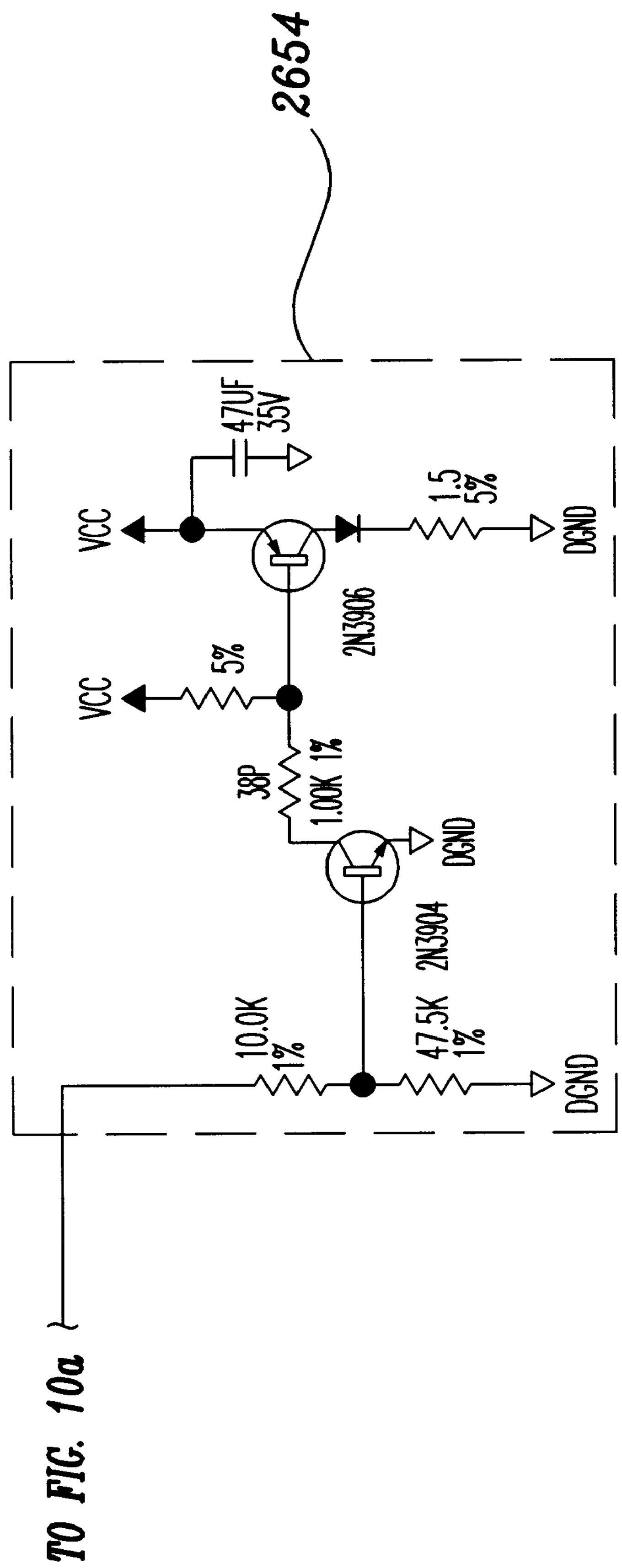

FIG. 9 illustrates a flow diagram of software operating a microcontroller which is a part of receiver 2516 for receiving output signals from an IR decoder circuit which receives IR data streams from the transmitter 2502 of FIG. 2. Upon the initial power-on reset of the microcontroller, the input/output ports are initialized at step 2608, the key received flag is cleared at step 2610, the idle flag is set at step 2612 and the port B interrupt is enabled at step 2614. At step 2616, the microcontroller begins looking for a flag indicating that a data stream has been received (hereinafter referred to as key received). If no key received flag has been set indicating that no data stream has been received, step 2616 proceeds to time out a period of time, called an abort time out, corresponding to the maximum permissible time between a primary data stream and an alternate data stream which would be considered a valid transmission. If this period of time expires, the microcontroller proceeds to step 2620 to set the idle flag and again await for a data stream and the setting of a key received flag at step 2616. If the abort time out has not expired, step 2618 proceeds back to step 2616 and if the received flag key is again set, the microcontroller proceeds to step 2622 where the abort time out is restarted (to one second, for example) and then to step 2624 where the key received flag is reset. If the idle flag has been previously set, step 2626 clears the idle flag by proceeding to step 2628, saves the current key code at step 2630 and waits for the next key received flag at step 2616. If the idle flag has not been set, the microcontroller determines whether the data stream (called a key code) is a valid one at step 2632. If it is not, the idle flag is set by step 2634 and the program returns to wait for the next data stream to be received. Otherwise, the function code of the data stream (whether it is primary or alternate), is compared to the last function code at step 2636. If it is not the same, the microcontroller proceeds to step 2638 where the current function code is saved and then returns to step 2616 to await the next data stream. If the function code number is the same as the last function code, step 2640 determines whether the alternate bit has been changed. If it has, step 2642 saves the current function or key code and step 2644 reports the key to the main CPU of the system 2518 by providing functional control signals thereto. If no alternative bit is found, the current function code is saved at step 2638 to compare it to the next function code but no reporting to the main CPU is made and the microcontroller returns to step 2616 waiting for the next key received flag to be set.

FIG. 10 is another preferred embodiment of an infrared remote control transmitter employing alternate codes. In contrast to FIG. 2, which employs the software of FIGS. 6≧18 to control microcontroller 2520 to generate the alternate codes, FIG. 10 illustrates the use of logic circuitry 2646 to alternate between two different system codes on successive transmissions for providing signals to be received by a receiver for controlling an ophthalmic microsurgical system. As in FIG. 2, keypad 2504 of FIG. 10 provides up/down signals which are generated by depressing keys on the keypad 2504 to close corresponding switches. These up/down signals are provided to a remote control encoder chip such as a Phillips SA3010. Microcontroller 2652 is responsive to the keypad 2604 to transmit infrared data streams generated by an IR transmitting circuit 2654. This encoder chip has an additional set of inputs which allow selection of one of several system codes. The particular system code to be transmitted is controlled by switches 2648 and 2650. Any logic circuits such as the low-power CMOS circuitry illustrated in FIG. 10 may be used to alternate between two different system codes on successive key transmissions.

Switches 2648 and 2650 are alternatively closed according to the following logic. From an idle condition, flip-flop 2656 is in a reset condition and both switches 2660 and 2662 are open. Switch 2648 is open and switch 2650 is closed. In the idle condition, capacitor 2658 has no charge thereon. When a key is depressed and data begins being generated, flip-flop 2656 is clocked high by the first transmission of the data which closes switch 2660. Switch 2662 closes only during data transmissions to prevent the charging of capacitor 2658. When a data stream ends, switch 2662 opens and capacitor 2658 begins charging. Capacitor 2658 in combination with resistor 2666 have a time constant which is longer than a single transmission of 16 bits and shorter than the auto repeat timeout between transmissions. For example, if a single bit transmission is 19.2 milliseconds and the auto repeat timeout is 200 milliseconds, the time constant would be longer than 19.2 milliseconds and shorter than 200 milliseconds. When the capacitor 2658 is charged, it sets the Schmidt trigger 2664 to clear flip-flop 2656 thereby changing the state of flip-flop 2668 to toggle switches 2648 and 2650. The next data stream again clocks the flip-flop 2656 to its high condition and closes switch 2662 thereby beginning the logic circuit operation over again eventually resulting in the clocking of flip-flop 2668 to close the open switch and open the closed switch of the switch set 2648 and 2650.

In view of the above, it will be seen that the several objects of the invention are achieved and other advantageous results attained.

As various changes could be made in the above products without departing from the scope of the invention, it is intended that all matter contained in the above description and shown in the accompanying drawings shall be interpreted as illustrative and not in a limiting sense.

What is claimed is:

1. An apparatus for use by an operator for remotely controlling a system comprising:

a transmitter having a keypad having keys which the operator controls by activating the keys, the transmitter being responsive to the keypad for transmitting first and second signals, each of the signals including a function code defined by the particular key activated by the operator and including an additional code wherein the function code of the first and second signals is the same and wherein the additional code of the first signal is different from the additional code of the second signal; and a receiver for receiving the first and second signals transmitted by the transmitter, the receiver associated with the system for providing functional control signals to the system for controlling functions of the system according to the function codes transmitted by the transmitter, the receiver providing functional control signals to the system only when the additional code of the first signal is different from the additional code of the second signal.

2. The apparatus of claim 1 wherein the transmitter transmits third and fourth signals after the first and second signals, each of the third and fourth signals including the function code of the first and second signals and including an additional code, wherein the third signal has the same additional code as the first signal and the fourth signal has the same additional code as the second signal.

3. The apparatus of claim 1 wherein the transmitter transmits successive data streams, each data stream having the function code and a logically related form of the function code.

4. The apparatus of claim 3 wherein each data stream transmitted by the transmitter comprises a preamble, a function code, the additional code, an inverted form of the function code and a checksum.

5. The apparatus of claim 1 wherein the transmitter comprises:

a controller connected to the keypad and generating first and second data streams in response to one or more keys being activated by the operator, each of the data streams including the function code corresponding to the activated key and including the additional code; and a transmitting circuit responsive to the controller and receiving the first and second data streams, said transmitting circuit transmitting remote control signals corresponding to the first and second data streams whereby the transmitted remote control signals include the function code corresponding to the activated key and successively different additional codes corresponding to the additional codes of the first and second signals.

6. The apparatus of claim 1 wherein the transmitter comprises:

a controller connected to the keypad and generating data streams in response to one or more keys being activated by the operator, each of the data streams including the function code corresponding to the activated key and including the additional code;

a logic circuit connected to the controller for defining the additional code, said logic circuit responsive to each data stream for defining alternate additional codes; and a transmitting circuit responsive to the controller and receiving the data streams, said transmitting circuit transmitting remote control signals corresponding to the data streams whereby the transmitted remote control signals include the function code corresponding to the activated key and successively different additional codes corresponding to the additional codes defined by the logic circuit.

7. The apparatus of claim 1 wherein the receiver comprises:

a controller receiving a signal corresponding to the first and second data streams, each of the data streams including the function code corresponding to the activated key and including the additional code, said controller providing the functional control signals corresponding to the function code in response to the received first and second data streams.

8. A remote control transmitter for use by an operator comprising:

a keypad having keys which may be selectively activated by the operator;

a controller connected to the keypad and generating first and second signals in response to one or more keys being activated by the operator, each of the signals defining a code sequence including a function code corresponding to the activated key and including one of a plurality of additional codes wherein the function code of the first and second signals is the same and wherein the additional code of the first signal is different from the additional code of the second signal; and a transmitting circuit responsive to the controller and receiving the first and second signals, said transmitting circuit transmitting remote control signals corresponding to the first and second signals whereby the transmitted remote control signals include the function code corresponding to the activated key and successively different additional codes corresponding to the additional codes of the first and second signals.

9. An apparatus for remotely controlling a microsurgical ophthalmic system having a plurality of ophthalmic modules including a user interface module, said system comprising:

a transmitter having a keypad having keys which an operator controls by activating the keys, the transmitter being responsive to the keypad for transmitting first and second signals, each of the signals including a function code defined by the particular key depressed by the operator and including an additional code wherein the function code of the first and second signals is the same and wherein the additional code of the first signal is different from the additional code of the second signal; and a receiver for receiving the first and second signals transmitted by the transmitter, the receiver associated with the user interface module for providing functional control signals to the system for controlling the system according to the function codes transmitted by the transmitter, the receiver providing functional control signals to the ophthalmic modules via the interface module only when the additional code of the first signal is different from the additional code of the second signal.

* * * * *